US006673290B1

(12) United States Patent
Whayne et al.

(10) Patent No.: US 6,673,290 B1
(45) Date of Patent: Jan. 6, 2004

(54) ELECTRODE STRUCTURE FOR HEATING AND ABLATING TISSUE AND METHOD FOR MAKING AND ASSEMBLING THE SAME

(75) Inventors: James G. Whayne, Saratoga, CA (US); Yi Yang, San Francisco, CA (US); Patrick M. Owens, Cupertino, CA (US); David K. Swanson, Mountain View, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/189,918

(22) Filed: Nov. 12, 1998

(51) Int. Cl.[7] ............................... B29C 41/14
(52) U.S. Cl. ................ 264/135; 264/255; 264/275; 264/305; 264/317; 264/318; 264/DIG. 44
(58) Field of Search ................ 264/255, 135, 264/271.1, 265, 275, 305, 317, 318, DIG. 44

(56) References Cited

U.S. PATENT DOCUMENTS 2,285,502 A * 6/1942 Dreyfus ...................... 264/304
4,043,342 A   8/1977 Morrison, Jr. ........... 128/303.14
5,562,720 A  10/1996 Stern et al. ..................... 607/98
5,766,171 A   6/1998 Silvestrini ..................... 606/49
5,797,903 A * 8/1998 Swanson et al. ............... 606/34
5,891,135 A * 4/1999 Jackson et al. ................ 606/41
5,961,909 A * 10/1999 Iverson ........................ 264/219

FOREIGN PATENT DOCUMENTS

| DE | 686416       | 1/1940  |
| EP | 0 856 291 A2 | 8/1998  |
| FR | 651.829      | 2/1929  |
| WO | WO 95/05780  | 3/1995  |
| WO | WO 97/25918  | 7/1997  |
| WO | WO 98/58681  | 12/1998 |

* cited by examiner

Primary Examiner—Edmund H. Lee
(74) Attorney, Agent, or Firm—Bingham McCutchen LLP (57) ABSTRACT

Methods of manufacturing cellulosic structures, e.g., for use in expandable-collapsible electrode assemblies for diagnostic and/or therepeutic electrophysiology devices, are disclosed. One such preferred method includes providing a mandrel having a head portion and a neck portion, the head portion having an outer circumference greater than the neck portion, dipping the mandrel into a cellulosic substance, curing the cellulosic substance, and separating the mandrel from the cured cellulosic substance.

13 Claims, 9 Drawing Sheets

ELECTRODE STRUCTURE FOR HEATING AND ABLATING TISSUE AND METHOD FOR MAKING AND ASSEMBLING THE SAME

FIELD OF THE INVENTION

The invention relates, in general, to electrode structures deployable into interior regions of the body, and, in particular, to electrode structures deployable into the heart for diagnosis and treatment of cardiac conditions.

BACKGROUND OF THE INVENTION

It is known that the effective treatment of cardiac arrhythmias requires creating tissue lesions having a diversity of different geometries and characteristics, depending upon the particular physiology of the arrhythmia to be treated. This recognition is discussed in U.S. patent application Ser. No. 08/631,356, filed Apr. 12, 1996, and Provisional Application Serial Nos. 60/010,223, 60/010,225, and 60/010,354, which were filed on Jan. 19, 1996. These applications are fully incorporated herein by reference for all they disclose and describe.

As discussed therein, one proposed solution to the creation of diverse lesion characteristics is to use different forms of ablation energy, e.g., microwave, laser, ultrasound, and chemical ablation. However, these technologies are largely unproven for this purpose.

The use of active cooling in association with the transmission of DC or radio frequency ("RF") ablation energy is known to force the electrode-tissue interface to lower temperature values. As a result, the hottest tissue temperature region is shifted deeper into the tissue, which, in turn, shifts the boundary of the tissue rendered nonviable by ablation deeper into the tissue. An electrode that is actively cooled can be used to transmit more ablation energy into the tissue, compared to the same electrode that is not actively cooled. However, control of active cooling is required to keep maximum tissue temperatures safely below about 100° C., at which tissue desiccation or tissue boiling is known to occur.

The treatment of some cardiac arrhythmias requires creating significantly large and deep lesions or lesions having relatively large surface areas with shallow depths. A proposed solution to the creation of these larger lesions is the use of substantially larger electrodes than those commercially available. However, larger electrodes themselves pose problems of size and maneuverability, which weigh against safe and easy introduction of large electrodes through a vein or an artery, and into the heart.

In an effort to solve the problems of maneuverability and safe introduction, collapsible ablation structures have been developed. These structures are manipulated to a collapsed position during introduction and maneuvering, and to an expanded position during ablation of the desired heart tissue. Numerous examples of such structures are shown and described in the above-referenced application. A number of the collapsible ablation structures disclosed therein include a balloon with a microporous membrane or coating made of regenerated cellulose that is filled with a hypertonic solution such as saline. In particular, the hypertonic solution acts as both a current carrying means and an inflation medium for expanding the balloon.

A balloon coating made of regenerated cellulose is desirable because it is an ion-permeable material, allowing the ionic transfer of electrical energy from an electrode disposed in the balloon interior into a patient's bloodstream and/or body tissue, while preventing macromolecules, such as blood proteins, from passing into the balloon.

The regenerated cellulose coating also acts as a biocompatible barrier between the catheter components and the body tissue, thereby allowing the components to be made from less expensive materials that may be somewhat toxic, e.g., silver or copper. The regenerated cellulose acts as a biocompatible barrier because it increases the diffusional distance to the body tissue and reduces the percentage of metallic surface directly and indirectly exposed to the tissue.

A problem with regenerated cellulose is that it is not known to be formable or moldable into a three-dimensional body structure such as that required for proper lesion creation. Also, regenerated cellulose is not known to be formable with operative elements, e.g., temperatures sensors, embedded therein, or formable so as to have a smooth exterior, as required for a tissue-contacting electrode body structure.

It would be desirable, therefore, to provide a method for manufacturing a three-dimensional electrode body structure made of regenerated cellulose.

During minimally-invasive diagnostic and therapeutic cardiac procedures such as endocardial mapping and ablating, the heart muscles continuously expand and contract with the beating of the heart, i.e., heart diastole and heart systole. When deployed in this environment, an catheter electrode assembly is subject to alternate cycles of contraction and expansion. The surface pressure of the electrode assembly against the moving endocardium can continuously vary, complicating the task of performing the diagnostic and/or therapeutic procedure desired.

A need therefore exists for a means for continuously urging the electrode assembly against the endocardium and for maintaining a constant surface pressure, despite contraction and expansion of the heart.

A need also exists for a means of evaluating the sufficiency of the surface contact of the electrode assembly with the endocardium so the operating physician will know ahead of time what the potential for success is for the diagnostic or therapeutic procedure to be performed on the heart.

SUMMARY OF THE INVENTION

According to one aspect of the invention, methods of manufacturing cellulosic structures, such as, e.g., for use in expandable-collapsible electrode assemblies for diagnostic and/or therapeutic electrophysiology devices, are disclosed. One such preferred method includes providing a mandrel having a head portion and a neck portion, the head portion having an outer circumference greater than the neck portion, dipping the mandrel into a cellulosic substance, curing the cellulosic substance, and separating the mandrel from the cured cellulosic substance.

According to a separate aspect of the invention, an electrode assembly is provided, which includes an expandable-collapsible body and a biasing device adapted to resiliently urge a distal portion of the body against adjacent body tissue.

According to yet another aspect of the invention, an electrode assembly is provided, which includes a regenerated cellulosic body substantially enclosing an interior area, a center support disposed in the interior area, and an electrode disposed on the center support.

Other, more particular features and advantages of the inventions are set forth in the following detailed description and drawings.

BRIEF DESCRIPTION OF THE DRAWINGS

The drawings illustrate both the design and utility of preferred embodiments of the present invention, in which similar elements are referred to by common reference numbers, wherein.

DESCRIPTION OF THE PREFERRED EMBODIMENTS

Figure 1A:
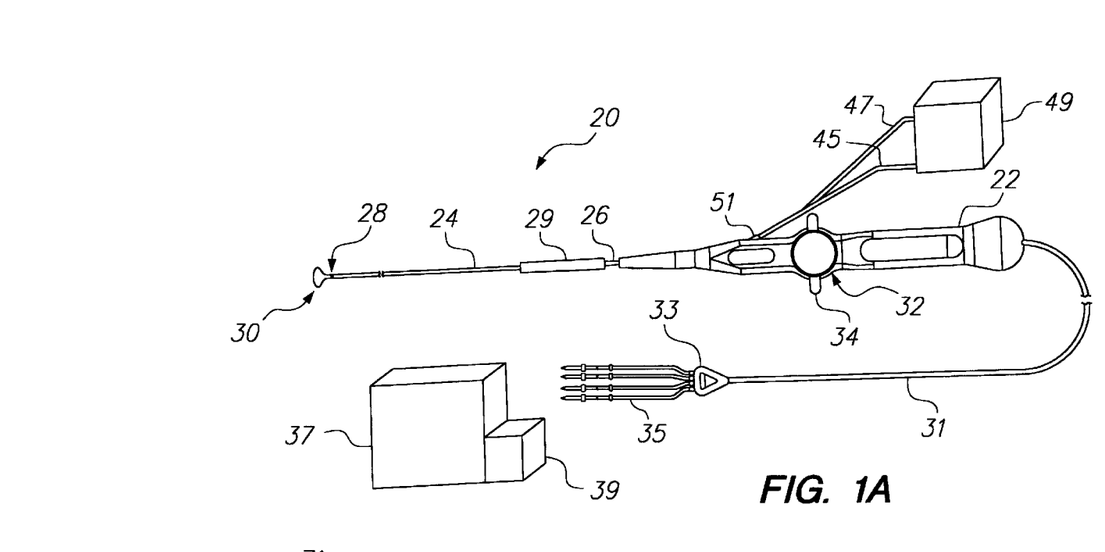
FIG. 1A is a perspective view of an embodiment of a system for ablating heart tissue and illustrates an exemplary catheter assembly, including an expandable electrode structure, for ablating heart tissue.

With reference to FIG. 1A, a steerable catheter 20 for performing ablation on cardiac tissue is shown. The catheter 20 includes a handle 22 and a guide tube 24. The guide tube 24 has a proximal end 26 attached to the handle 22 and a distal portion 28 that carries an electrode structure 30. A retractable sheath 29 may cover the electrode structure 30, when collapsed, to protect the electrode structure.

The distal portion 28 of the guide tube 24 may include a series of ring electrodes (not shown) for sensing electrograms to locate the region of the myocardial tissue that is to be ablated.

It should be appreciated that the invention is applicable for use in other tissue ablation applications such as, but not by way of limitation, ablating tissue in the prostate, brain, gall bladder, and uterus, and using systems that are not necessarily catheter-based.

A cable 31 preferably extends from the rear of the handle 22 and includes plugs 33 for connecting the catheter 20 to a source of ablation energy. The ablation energy is conveyed through wires 35 in the cable 31 to the electrode structure 30 for creating lesions in the myocardial tissue.

Although the type of ablation energy used can vary, radio frequency ("RF") electromagnetic energy is preferably used in the illustrated embodiments. The energy source is a RF generator 37 that preferably delivers up to about 150 watts of power at a frequency of about 350 to 700 kHz, preferably about 500 kHz.

A controller 39 is associated with the generator, either as an integrated unit or as a separate interface box for governing the delivery of RF ablation energy to the electrode structure 30.

The handle 22 encloses a steering mechanism 32 for maneuvering the distal portion 28 of the guide 24 through the vasculature of the patient's body. Left and right steering wires 41, 43 (FIGS. 8A, 15) extend through the guide tube 24 for interconnecting the steering lever 34 of the steering mechanism 32 to the distal portion 28. Rotation of the steering lever 34 to the left pulls on the left steering wire 41, causing the distal portion 28, including the electrode structure 30, to bend to the left. Rotation of the steering lever 34 to the right pulls on the right steering wire 43, causing distal portion 28 and electrode structure 30 to bend to the right.

In use, a physician holds the catheter handle 22 and introduces the catheter 20 through a main vein or artery, typically femoral, into the interior region of the heart near where the myocardial tissue is to be diagnosed and/or treated. The physician then further steers the distal portion 28 of the catheter 20 by means of the steering lever 34, to place the electrode structure 30 into contact with the tissue that is to be diagnosed and/or treated.

Figure 2:
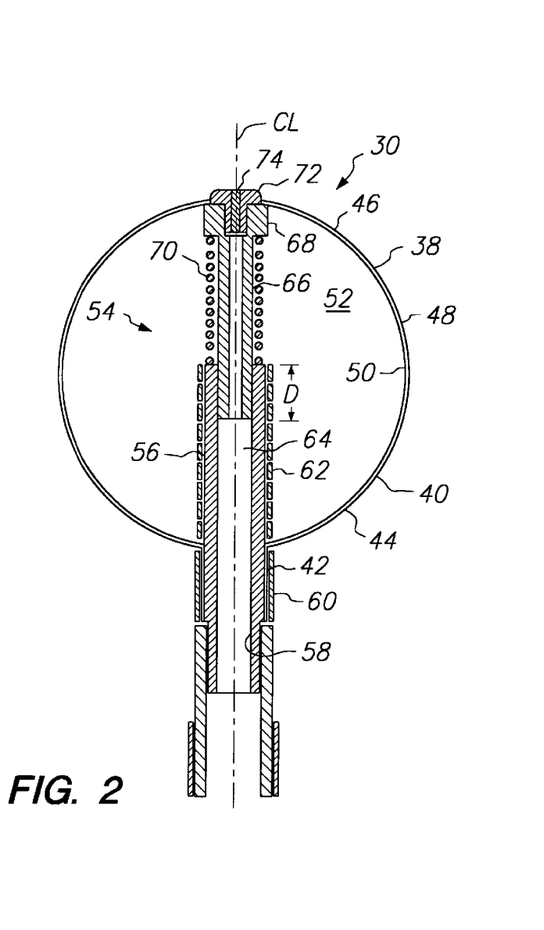
FIG. 2 is an enlarged cross-sectional view of an electrode structure constructed in accordance with an embodiment of the invention.

With reference to FIG. 2, the electrode structure 30, which is constructed in accordance with an embodiment of the invention, will now be described. The electrode structure 30 includes an expandable and collapsible body or balloon 38 made of regenerated cellulose. The body 38 preferably includes microsize pores having a size that allows ionic transport, but prevents the ingress of blood cells, infectious agents such as viruses and bacteria, and large biological molecules such as proteins.

The electrode body 38 includes a generally spherical head portion 40 and a relatively short, generally tubular neck portion 42. The relatively short length of the neck portion 42 gives the electrode structure 30 a compact configuration that can be easily maneuvered in the patient's body. The head portion 40 has a proximal region 44 and a distal region 46. The distal region 46 is preferably porous because this region is the preferred region of the body 38 for contacting myocardial tissue for ablation. One way to provide a porous distal region 46 is by masking an outer surface of the rest of the body 38 with a non-porous material or primer. The body has an inner surface 50 that surrounds an interior 52.

The body 38 is supported and attached to the distal portion 28 of the catheter 20 by a balloon support assembly 54. The balloon support assembly 54 includes a generally tubular receiver 56 having a proximal region and a distal region. The proximal region has a reduced-diameter portion 58 that fits snugly within the distal portion 28 of the guide tube 24 and is affixed to an inner wall of the guide tube 24 with an affixant such as cyanoacrylate.

Beyond the distal portion 28 of the guide tube 24, the receiver 56 carries a ring electrode 60 used for pacing myocardial tissue. In an alternative embodiment, the element 60 may be an anchor or connecting collar used to attach the electrode body 38 to the distal portion 28 of the guide tube. The electrode body 38 is attached near the distal portion 28 of the guide tube 24 by sandwiching the neck portion 42 of the body 38 between an inner surface of the ring electrode 60 and an outer surface of the receiver 56. Mechanical bonding means and/or an adhesive, e.g., cyanoacrylate, are used to ensure the attachment.

In the interior 52 of the body 38, the proximal region of the receiver 56 carries an electrode 62. A signal wire (not shown) extends through a tubular chamber 64 of the receiver 56 and through the guide tube 24 for electrically coupling the electrode 62 to the RF generator. The receiver 56 slidably receives a tubular plunger or shaft 66 that axially reciprocates within the tubular chamber 64. The shaft 66 has a proximal region that slides within the tubular chamber 64 and a distal region that includes a support head 68. The support head 68 of the shaft 66 includes a circular recess.

A spring coil 70 is carried along the outside of the shaft 66. The location of the shaft 66 within the spring 70 permits controlled axial movement of the distal region 46 of the body 38 with respect to the neck portion 42, and limits lateral movement.

Because the body 70 is inherently flexible, it is important for the body 70 to have some lateral and axial stiffness. Maintaining lateral stiffness allows the electrode structure 30 to be remotely steered better and torqued into the desired location within the patient's body.

The spring 70 has a fixed spring constant that does not vary with compression. The spring constant of the coil 70 determines the force required to compress the distal region 46 of the body 38. The spring constant can be tailored to account for the motion of the heart and maintain the desired amount of surface area of the balloon in contact with the myocardial tissue. Less surface area may be achieved with an axially stiffer spring while larger surface area may be achieved with a less stiff spring. Controlling the surface area in contact with the myocardial tissue controls the characteristics of the resulting lesion(s). The spring 70 may also be electrically conductive so that it functions as an electrode.

The body 38, receiver 56, reciprocating shaft 66, and spring 70 include respective longitudinal axes that are coaxial with one another. The resulting axis is represented in the drawings as CL.

The distal region 46 of the body 38 includes a hole that, in conjunction with the recess of the shaft head 68, receives a pacing electrode 72 and temperature sensor 74. Although the pacing electrode 72 and temperature sensor 74 are shown on the outside of the distal region 46 of the body 38, in an alternative embodiment, the pacing electrode 72 and temperature sensor 74 may be on the other side of the distal region 46 of the body 38, within the interior 52 of the body 38. The temperature sensor 74 is housed by the pacing electrode 72. An immediate portion of the distal region 46 of the body 38 surrounding the hole is attached to a distal part of the balloon support assembly 54 by sandwiching it between, and affixing it to, the pacing electrode 72 and the shaft head 68. An affixant such cyanoacrylate is used for affixing this portion of the body 38 to the pacing electrode 72 and shaft head 58. The temperature sensor 74 may consist of a thermistor, thermocouple, or the like. The pacing electrode 72 a lead wire and the temperature sensor 74 include a pair of lead wires, all of which pass through the balloon support assembly 54 and guide tube 24, back to the handle 22 for electrical connection to the cable 31. The controller 39 preferably controls the energy power supply, i.e., generator, in response to the sensed temperature.

Figure 1B:
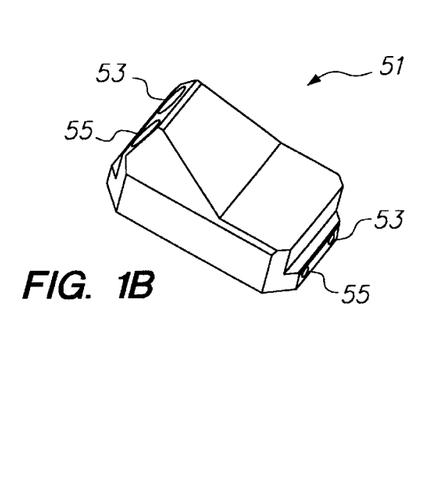
FIG. 1B is a perspective view of a lumen guide assembly of the catheter assembly illustrated in FIG. 1A.

With reference to FIG. 1A and 1B, the catheter 20 includes an input or infusion lumen 45 and an output or venting lumen 47 for adding and removing an electrically conductive fluid medium to and from the interior 52 of the body 38. A lumen guide assembly 51 in the handle 22 guides the lumens 45, 47 away from the handle where the lumens 45, 47 exit the handle 22. The guide assembly 51 includes hollow guides 53, 55 that receive the lumens 45, 47 and guide the lumens 45, 47 away from the handle 22.

The fluid medium is preferably a hypertonic saline solution having sodium chloride, i.e., about 9% weight by volume. A hypertonic potassium chloride solution may also be used; however, this fluid medium requires close monitoring of ionic transport through the pores to ensure potassium overload does not occur.

Each lumen 45, 47 forms a fluid pressure transmitting conduit that communicates with the interior 52 of the body 38. The lumens 45, 47 extend from a pressure control device 49 (FIG. 1A) to the interior. 52 of the body 38, through the guide tube 24. The pressure control device 49 is used to control the fluid pressure within the interior 52 of the body 38.

Imparting a positive fluid pressure with the pressure control device 49 causes the body 38 to expand or inflate from a normal, low profile condition to an enlarged, expanded operating condition. The inflating body 38 deploys outward, assuming a prescribed three-dimensional shape. The shape can vary, depending upon the pre-molded configuration of the body 38. The inflation is conducted to the extent that the body 38 is filled and expanded, but not stretched. Due to the pliant nature of the body 38, the body 38, when inflated, naturally conforms to the topography of the endocardial surface next to it. It has been recognized by the inventors that a less than fully expanded body condition adapts and conforms better to the surrounding heart tissue.

The lumens 45, 47 allow air in the interior 52c to be purged from the structure 120 and limit the pressure inside the electrode structure 120.

The pressure control device 49 may be controlled to release or vent fluid from the interior 52, through an inflation or venting lumen. This causes the body 38 to collapse into a deflated condition, and depending on the catheter design, may be retractable back into the catheter.

Figure 1C:
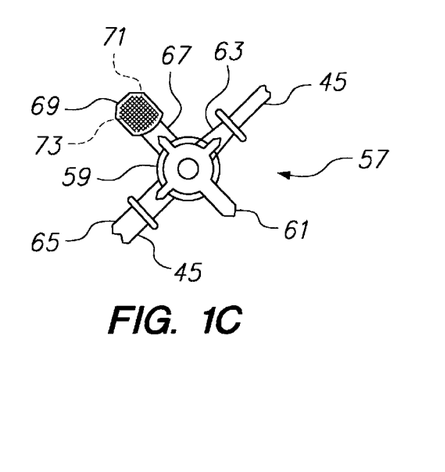
FIG. 1C is a top view of an embodiment of a pressure-relief mechanism for the expandable electrode structure.

With reference to FIG. 1C, the inflation lumen 45 may include a pressure-relief mechanism 57 between the catheter 22 and the pressure control device 49 to inhibit over inflating the body 38. The pressure-relief mechanism 57 includes a hollow cylindrical base 59 in which a three-way stopcock 61 is rotatably engaged. The inflation lumen 45 communicates with the hollow cylindrical base 59 through first and second main tubes 63, 65. A valve tube 67 is in communication with the hollow cyclindrical base 59 and carries a pressure-relief valve 69. The pressure-relief valve 69 is operatively associated with the valve tube 67 through a spring 71 and a mount 73. The stiffness of the spring 71 determines the relief pressure in the pressure-relief valve 69. This pressure is preferably between 10–15 psi. When the pressure in the interior 52 exceeds a predetermined threshold, as controlled by the stiffness of the spring 71, the pressure-relief valve 69 opens, releasing or venting fluid from the interior 52. The three-way stopcock 61 can be rotated for controlling the communication paths of the mechanism 57. In an alternative embodiment, the pressure-relief mechanism 57 may be incorporated into the venting lumen 47.

Alternatively, the movable sheath 29 controlled by a retraction mechanism may be used to selectively enclose the body 38 before and after use, during insertion into and retraction from the patient's body. The retraction mechanism is retracted to free the body 38 for inflation and use.

When the body 38 is in its normal, low profile condition, the body 38 maintains a standard 6–10 French size. When in its inflated condition, the same body 38 has an significantly enlarged dimension ranging from approximately 7 mm to 20 mm.

The catheter 20 and electrode structure 30 just described is ideally suited for ablating myocardial tissue within the heart. A physician moves the catheter tube 24 through a main vein or artery into a heart chamber, while the expandable-collapsible body 38 of the electrode structure 30 is in its low profile geometry. Once inside the desired heart chamber, the expandable-collapsible body 38 is enlarged into its expanded geometry with the pressure control device 49, and the distal region 46 containing pores is placed into contact with the targeted region of endocardial tissue, which was preferably determined by a mapping procedure previously performed by the catheter 20 for locating aberrant electrical pathways in the endocardial tissue.

Due largely to mass concentration differentials across the pores in the distal region 46, ions in the medium will pass into the pores because of concentration differential-driven diffusion. Ion diffusion through the pores will continue as long as a concentration gradient is maintained across the body 38. The ions contained in the pores provide the means to conduct current across the body 38.

RF energy is conveyed from the generator 37 to the electrode 62, as governed by the controller 39. When RF voltage is applied to the electrode 62, electric current is carried by the ions in the fluid medium to the ions within the pores. The RF currents provided by the ions result in no net diffusion of ions, as would occur if a DC voltage were applied. The ions move slightly back and forth during the RF frequency application. This ionic movement and current flow in response to the applied RF field does not require perfusion of liquid in the medium through the pores.

The ions convey RF energy through the pores into tissue to a return electrode, which is typically an external patch electrode, i.e., a unipolar arrangement. Alternatively, the transmitted energy can pass through tissue to an adjacent electrode in the heart chamber, i.e, forming a bipolar arrangement. The RF energy heats the tissue, mostly ohmically, forming the desired lesion.

The pacing electrodes 60, 72 of the electrode structure 30 can be used in association with a conventional pacing apparatus (not shown) for pacing the heart or acquiring electrograms in a conventional fashion. The pacing apparatus is electrically coupled to the electrical wires of the cable to provide a pacing signal to a selected one of the electrodes 60, 72, generating depolarization foci at selected sites within the heart. The electrodes 60, 72 may also serve to sense the resulting electrical events for the creation of electrograms. Used in this fashion, the electrode structure 30 can accommodate both pace mapping and entrainment pacing techniques.

It is important for the distal region 46 of the body 38 to be in good contact with the myocardial tissue for the above therapeutic and diagnostic procedures, and for accurately determining the temperature of the myocardial tissue to be treated. This is difficult because during these procedures the heart muscles continuously expand and contract with the beating of the heart, i.e., during heart diastole and systole. When expanded, the body 38 is subject to alternate cycles of contraction and expansion. The surface pressure of the distal region 46 against the moving endocardium continuously varies, complicating the task of accurately performing the above-described procedures. The distal region 46 can also slip along the constantly moving endocardial surface.

The spring 70, receiver 56, and reciprocating shaft 66 form a biasing device that counteracts this phenomenon by continuously urging the distal region 46 of the body 38 in an axial direction against the endocardium and maintaining a constant surface pressure, despite the contraction and expansion of the heart.

During heart systole in the heart chamber, the distal region 46 experiences compression. Movement of the distal region 46 towards the receiver 56 axially compresses the spring 70. When compressed, the spring 70 urges the head 68 of the shaft 66 against the distal region 46, pushing the distal region 46 forward. The fluid pressure in the interior 52 of the body 38 also provides a radially outward force against the endocardial surface. The spring 70 dampens and resists the movement of the endocardium, holding the distal region 46 against the endocardium. This maintains contact pressure between the distal region 46 and the endocardium during heart systole.

When the heart chamber expands, the spring 70 urges the distal region 46 forward, urging the distal region 46 towards its original shape. Thus, the spring 70 maintains contact pressure between the distal region 46 and the surrounding, moving endocardium during heart diastole.

Enabling the distal region 46 of the body 38 to compress axially allows a larger surface area to be positioned into contact with myocardial tissue as the geometry of the body surface changes because of the moving heart, and allows the functionality of the electrode structure 30 to be maintained, i.e., the ability to steer, torque, and collapse the electrode structure.

Because the spring 70 is a constant force spring, a relatively constant surface pressure is established and maintained between the distal region 46 of the body 38 and the surrounding endocardium when the distal region 46 is compressed.

In order to determine the sufficiency of tissue contact obtained by the distal region 46 of the body 38, the electrode structure may include a mechanism for quantifying the degree of tissue contact with the distal region 46, i.e. a tissue contact evaluating mechanism.

Figure 3:
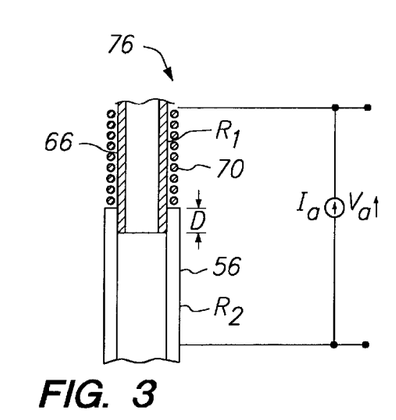
FIG. 3 is a partial, cut-away side view of a shaft and a receiver of the electrode structure illustrated in FIG. 2, and illustrates an embodiment of a mechanism for determining the displacement of the shaft.

With reference to FIG. 3, the tissue contact evaluating mechanism includes a displacement determining mechanism 76. The shaft displacement determining mechanism includes an electrical circuit having a variable resistor with a resistance $R_{var}$, a current source with a current $I_a$, and a measured voltage $V_a$.

The resistance $R_{var}$ of the variable resistor depends on the resistance of $R_1$ and $R_2$, where $R_1$ is the resistance of the reciprocating shaft 66 and $R_2$ is the resistance of the receiver 56, and the displacement of D of the shaft 66. The resistivities of the receiver 56 and the shaft 66, $R_1$, $R_2$, respectively, must be chosen to permit adequate resolution of resistance measurements. Accordingly, the desired resistivities are obtained by constructing the receiver 56 and shaft 66 from conductive metals, or doped thermoplastics or thermosets. The shaft 66 is configured to contact an interior surface of the receiver 56 upon displacement of the shaft 66. Separate wires of the electrical circuit are attached to the receiver 56 and shaft 66.

Resistances $R_{var}$ are measured and correlated with different displacements of the shaft 66.

Ohm's law provides:

$$V_a = I_a R_{var}.$$

Thus, displacement of the shaft D is determined by measuring voltage $V_a$, because measured voltage $V_a$ yields resistance $R_{var}$, which yields displacement D from previous correlations.

Figure 4:
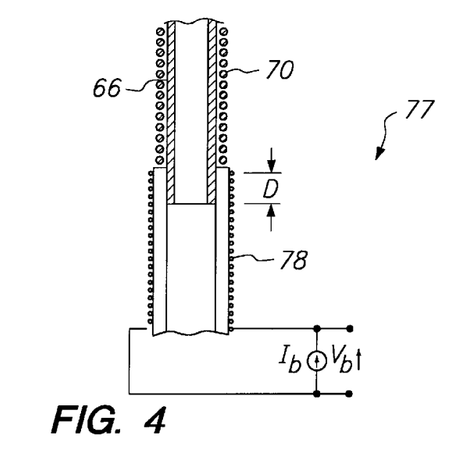
FIG. 4 is a partial, cut-away side view of a shaft and a receiver of the electrode structure illustrated in FIG. 2, and illustrates an alternative embodiment of a mechanism for determining the displacement of the shaft.

With reference to FIG. 4, a shaft displacement determining mechanism 77, constructed in accordance with another embodiment of the invention, will now be described. The shaft displacement determining mechanism 77 includes an electrical circuit having a solenoid 78 with an inductance L, a sinusoidal current $I_b$ having a frequency less than 100 kHz, and a measured voltage $V_b$. The shaft 66 is completely ferromagnetic or includes a substantial ferromagnetic portion so that displacement of the shaft 66 causes a measurable voltage V to develop across the solenoid, and a resulting change in current di over a discrete time period dt. The voltage V across the solenoid is governed by the following equation:

$$V = L(di/dt),$$

where the inductance L of the solenoid is correlated with numerous displacements D of the shaft so that the displacement D of the shaft 66 can be determined based on L.

By measuring the voltage V across the solenoid, the displacement D of the shaft 66 can be determined.

Regardless of the means for determining the displacement D of the shaft 46, the pressure P on the distal region 46 of the body 38 is determined as follows:

$$P = F/A,$$

where F is the compressive force on the distal region 46 of the body 38, and A is the surface area of the distal region 46. The surface area A of the distal region in contact with the myocardial tissue depends on the displacement of the shaft.

Numerous values for surface area A are correlated for various shaft displacements. Thus, the surface area A will be known for a given shaft displacement D.

Because $F = kD$, where k is the known spring constant of the spring 70, P can be rewritten as:

$$P = (kD)/A$$

Thus, by measuring the voltage V, the surface area A, and the axial pressure P at the distal region 46 of the body 38 can be determined. The surface area A and axial pressure P can be compared to respective reference values to determine the sufficiency of the tissue contact at the distal region 46. Knowing the sufficiency of the tissue contact at the distal region 46 is important for a number of reasons such as determining whether the temperature sensor 74 is providing an accurate reading of the myocardial tissue, the electrode structure 30 needs to be re-positioned for pacing, ablating, and/or sensing, and the pacing, ablating and/or sensing potential prior to delivering energy.

Figure 5:
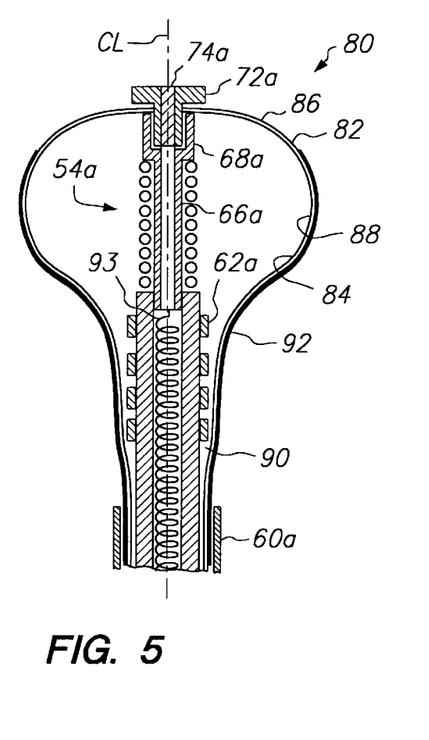
FIG. 5 is an enlarged cross-sectional view of an electrode structure constructed in accordance with another embodiment of the invention.

With reference to FIG. 5, an electrode structure 80, constructed in accordance with an additional embodiment of the invention will now be described. Where appropriate, like reference numbers with an "a" suffix have been used to indicate like parts of the embodiments for ease of understanding. The electrode structure 80 illustrated in FIG. 3 is different from the electrode structure 30 illustrated in FIG. 2 in that the electrode structure 80 includes an expandable-collapsible body 82 having a different configuration than that of expandable-collapsible body 38. The body 82 has a generally squashed tear-drop or pear shape. The body 82 includes a head portion 84 having a distal region 86 and proximal region 88. The distal region 86 of the head portion 84 is generally flat, increasing the surface area of the distal region 86, compared to distal region 46 of the body 38, for contacting myocardial tissue for ablation. A larger tissue contact surface area allows larger lesion creating capability. The body 82 also includes a slightly incurved neck portion 90. The incurved neck portion 90 has a relatively large radius of curvature. The relatively large radius of curvature in the neck portion 90 facilitates collapsing of the body 82 into a low profile for removal of the electrode structure 80 from the body.

The body 82 may also include a non-porous mask 92 along the neck portion 90 and the proximal region 88 of the head portion 84 to prevent ionic transport through an area of the body 82 where it is not required.

One or more signal wires 93 may be helically wound within the guide tube 24 and/or balloon support assembly 54 to allow for more unrestricted axial movement of the shaft 66a and the distal region 86 of the body 82. A straight wire is stiffer than a helically wound wire and inhibits the axial movement of the shaft 66a and the distal region 86 of the body 82.

Figure 6A:
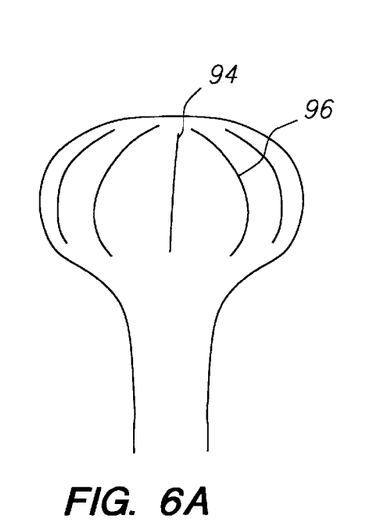
FIGS. 6A and 6B are an enlarged side elevational view and a top plan view, respectively, of an electrode structure constructed in accordance with a further preferred embodiment of the invention.
Figure 6B:
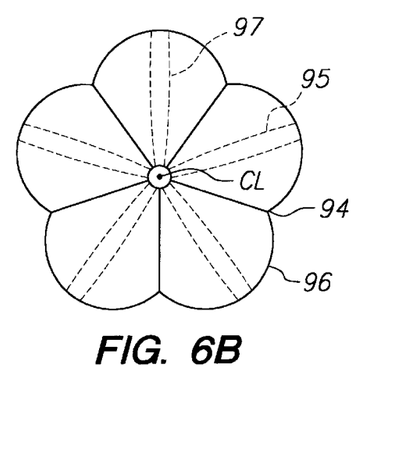

With reference to FIGS. 6A and 6B, in a preferred embodiment, the body 82 includes longitudinally disposed ridges 94 and bulbous regions 96. The bulbous regions 96 include a support rib assembly 95 having support ribs 97 to structurally reinforce the body 82. The support ribs 97 are longitudinally disposed with respect to a longitudinal axis CL of the body 82 and are preferably laminated with the body material. This construction facilitates collapsing of the body 82 in a predetermined and repeatable manner. The ridges 94 and bulbous regions 96 cause the body 82 to have a generally summer-squash shape.

The support ribs are preferably made of a casing paper such as grade 15254 casing paper sold by the Dexter Corporation of Windsor Locks, Conn. The casing paper is a medium weight hemp fiber tissue possessing multidirectional tensile strength. The casing paper has a basis weight of 25.4 g/m$^2$, a wet tensile strength of 1500 g/25 mm and 1200 g/25 mm, a wet grain ratio of 80%, a dry edge elongation of 5.9%, a dry center elongation of 4.4%, and an absorbency of 10 (25 mm water climb). The casing paper has a pore size larger than the pore size of the body material. This prevents the casing paper from interfering with the ion diffusion through the body 82.

When the fluid medium is removed from the interior 52*a* of the body 82, the body 82 naturally collapses inward at the longitudinally disposed ridges 94, and the bulbous regions 96 form folds that wrap around the balloon support in an overlapping manner.

Figure 7:
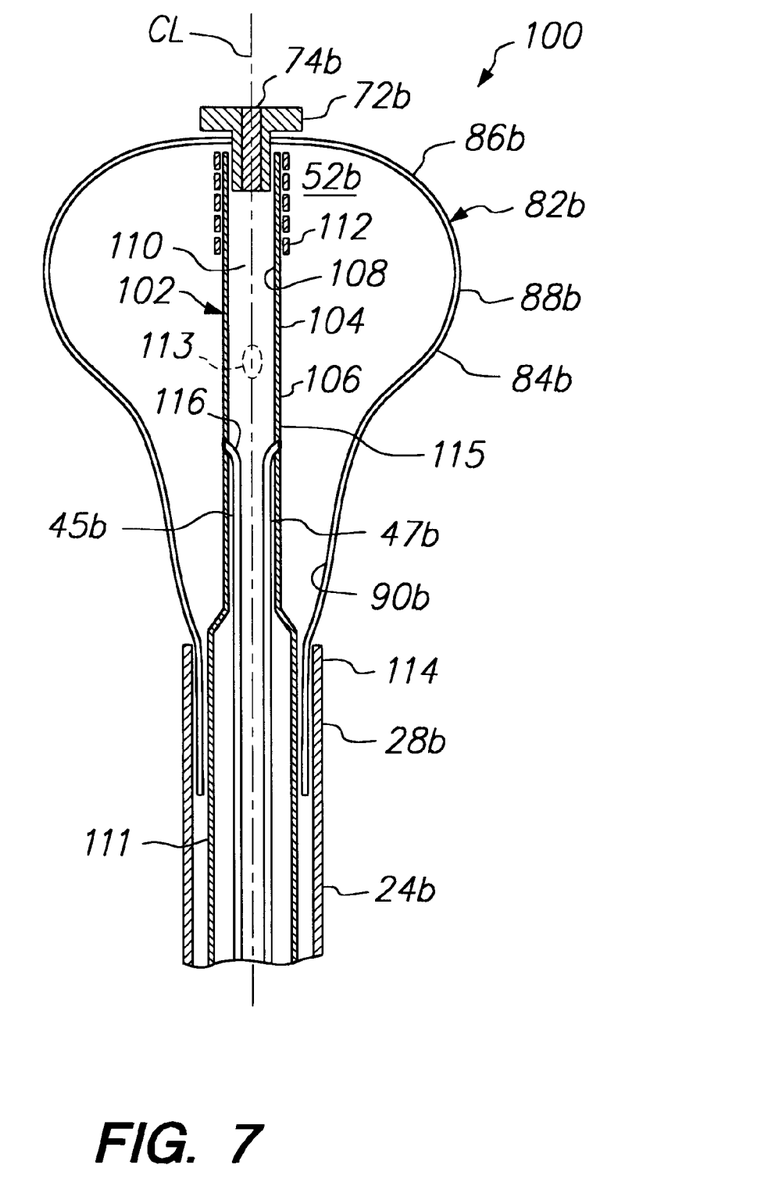
FIG. 7 is an enlarged cross-sectional view of an electrode structure constructed in accordance with an additional embodiment of the invention.
Figures 8A, 8B, 9A:
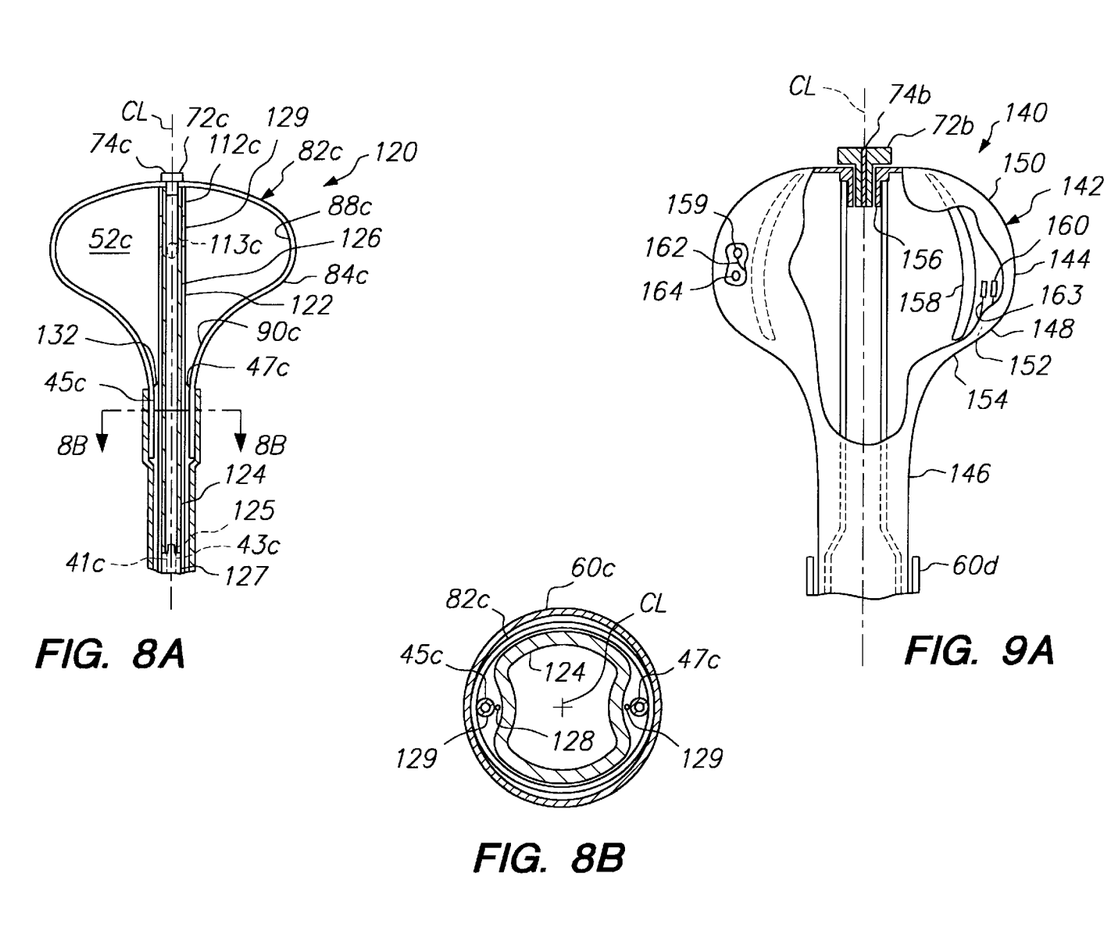
FIGS. 8A and 8B are an enlarged longitudinal cross-sectional view and an enlarged lateral cross-sectional view, respectively, of an electrode structure constructed in accordance with a further preferred embodiment of the invention.
FIG. 9A is an enlarged, partially cut-away side elevational view of an electrode structure constructed in accordance with yet another embodiment of the invention.
Figure 9B:
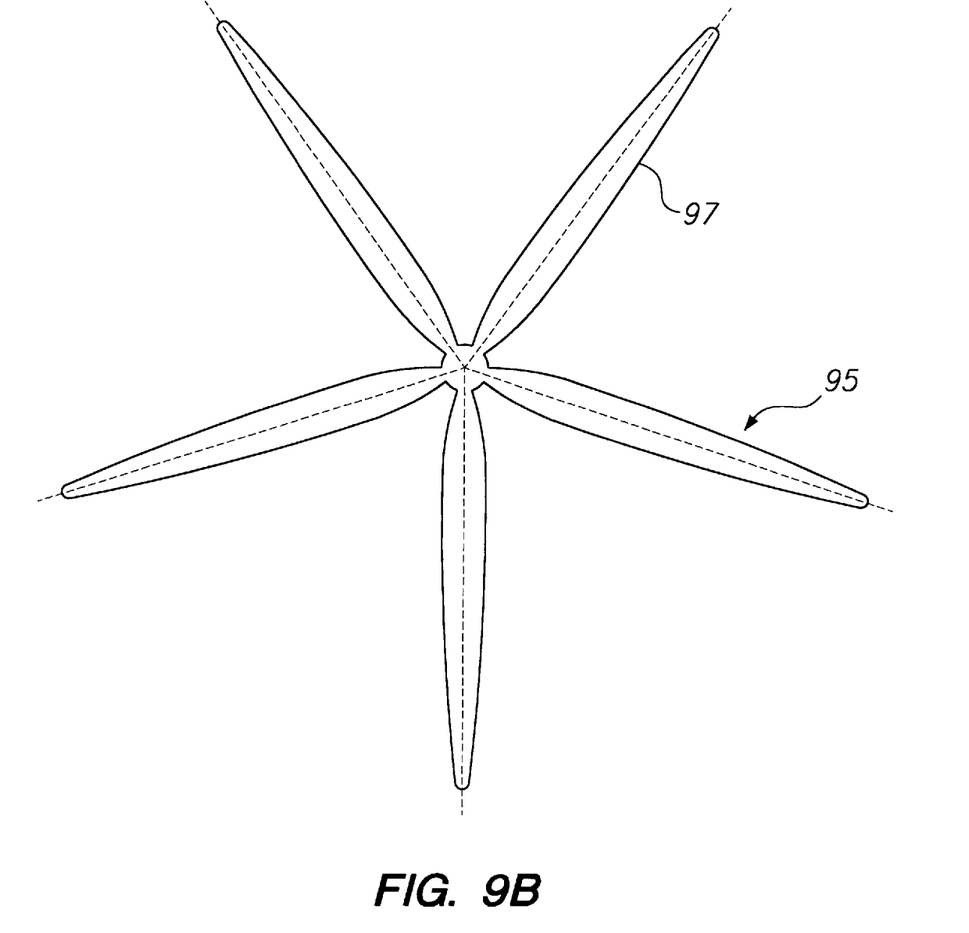
FIG. 9B is a top plan view of an embodiment of a rib support assembly illustrated in FIG. 9A.

FIGS. 7–9 illustrate additional embodiments of the electrode structure of the present invention. Where appropriate, like reference numbers with a "b", "c", and "d" suffix have been used in the respective figures to indicate like parts of the embodiments for ease of understanding.

With reference to FIG.7, an electrode structure 100, constructed in accordance with an additional embodiment of the invention is shown. The electrode structure 100 includes a tubular hollow balloon support 102. The balloon support 102 includes a wall 104 having an outer surface 106 and an inner surface 108. The inner surface 108 surrounds an interior chamber 110.

The balloon support 102 also includes a proximal region and a distal region. The distal region has a reduced-diameter portion 115 and the proximal region has an enlarged-diameter portion 111 that fits snugly within the distal portion 28*b* of the guide tube 24*b*.

The electrode body 82*b* is attached to the distal portion 28*b* of the guide tube 24*b* by sandwiching the neck portion 90*b* between an inner surface of the distal portion 28*b* of the guide tube 24*b* and an outer surface of the balloon support 102. The electrode body 82*b* may be further attached at this region with a mechanical bond and/or adhesive.

In the interior 52*b* of the body 82*b*, the distal region of the balloon support 102 carries an electrode 112. Signal wires (not shown) electrically couple the electrode 112 to the cable 31.

The body 82*b* and balloon support 102 include respective longitudinal axes that are coaxially aligned, forming a common longitudinal axis CL.

A temperature sensor 113 is located in the balloon support wall 104, partially exposed, near the center of the interior 52*b*, for determining the temperature of the fluid medium in the body 82*b*. The temperature sensor 113 may comprise a thermocouple, thermistor, or the like with a pair of lead wires (not shown) that pass through the balloon support 102 and guide tube 24*b*, back to the handle 22 for electrical connection to the cable 31.

A temperature sensor 113 is placed within the interior of the body or balloon 82*b* to complement the temperature sensor 74*b* positioned within the distal tip pacing electrode 72*b*. The temperature sensor 74*b* located at the distal end 86*b* of the body 82*b* provides accurate tissue temperature measurements, particularly when the body 82*b* is positioned such that the distal end 86*b* contacts tissue. Because of the large diameter of the inflated body 82*b*, the distal temperature sensor 74*b* does not contact tissue when the body 82*b* is positioned so that one side of the body 82b contacts tissue. A temperature sensor 113 located within the body 82*b* helps to give a more accurate tissue temperature measurement.

The controller regulates delivery of radiofrequency energy to the electrode 112 inside the body 82*b* based on the maximum temperature of the two temperature sensors 74*b*, 113. This enables more accurate temperature monitoring for all orientations of the body 82*b* relative to tissue.

Predictive temperature algorithms previously described may be employed to predict the maximum tissue temperature by comparing temperature measured at the distal tip 86*b* and within the body 82*b*. In addition, comparing measured temperature at the distal tip 86*b* and within the body 82*b* provides an estimate of the orientation of the body 82*b* relative to tissue. If the temperature at the distal tip 86*b* is significantly higher than that within the body 82*b*, the body 82*b* is end-on relative to tissue. If the temperature within the body 82*b* is higher than that at the distal tip 86*b*, the body 82*b* is oriented sideways relative to tissue.

A pair of lumens 45*b*, 47*b* extend through the guide tube 24*b* and balloon support 102, and terminate into respective open distal ends 116. The balloon support 102 includes a pair of opposing holes near the center of the interior 52*b* that receive the distal ends 116 of the lumens 45*b*, 47*b*. The lumens 45*b*, 47*b* convey the fluid medium to and from the interior 52*b* of the body 82*b*. Although a pair of lumens 45*b*, 47*b* are shown, the number of lumens and the junction location of the lumens 45*b*, 47*b* with the balloon support 102 may vary.

With reference to FIGS. 8A and 8B, an electrode structure 120, constructed in accordance with a preferred embodiment of the invention, is shown. The electrode structure 120 includes a tubular balloon support 122 having a hollow proximal portion 124 of an enlarged diameter and a distal portion 126 of a reduced diameter. The distal portion 125 of a steering wire assembly 127 including steering wires 41*c*, 43*c* is attached to the balloon support 122 at the proximal portion 124. The proximal portion 124 includes laterally incurved sections 128 on opposite sides of the balloon support 122. The laterally incurved sections 128 receive respective electrode wires 129 and lumens 45*c*, 47*c* that extend through the guide tube 24*c* and into the interior 52*c*, on the outside of the balloon support 122. The wires 129 extend from the electrode 112*c* and are connected to the cable 31. The lumens 45*c*, 47*c* terminate into open distal ends 132 in the interior 52*c*. The lumens 45*c*, 47*c* serve the same function as the aforementioned lumens illustrated in FIGS. 1 and 7.

With reference to FIG. 9A, an electrode structure 140, constructed in accordance with a further embodiment of the invention, is shown. The electrode structure 140 includes a body 142 with a similar configuration to the body 82 described above. The body 142 includes a head portion 144 and a neck portion 146. The head portion includes a proximal region 148 and a distal region 150. The body 142 also includes an inner surface 152 and an outer surface 154.

The distal region 150 includes a recessed portion 156 made of the same regenerated cellulosic substance as the body 142 and formed integrally therewith. The recessed portion 156 carries the pacing electrode 72*d* and the temperature sensor 74*d*. The pacing electrode 72*d* is affixed to the recessed portion 156 along its length and underside, i.e., where the pacing electrode 72*d* contacts the recessed portion 156, with an affixant such as cyanoacrylate. Providing a recessed portion 156 formed integrally with the body 142 and affixing the recessed portion 156 along its length and underside to the pacing electrode 72*d* ensures that the body 142 does not tear away from the distal portion of the balloon support 102*d*. The pacing electrode 72*d*, temperature sensor 74*d*, and balloon support 102d may also be formed integrally with the body 142.

A number of elements may also be formed integrally with the body 142. For example, support ribs 158, similar to the support ribs 97 described above in conjunction with FIGS. 6A and 6B, may be integrally formed with the body 142. The support ribs 158 may be made of a separate material such as casing paper, or, similar to the recessed portion 156, the support ribs 153 may be constructed of the same material as the body 142.

Operative elements other than the pacing electrode 72d and the temperature sensor 74d may also be integrally formed with or embedded at least partially within the body 142. For example, temperature sensors 159 and electrodes 160 may be formed integrally with the body 142.

The electrodes 160 are suitable for unipolar or bipolar sensing or pacing. The electrodes 160 are embedded in the body material so that they are able to make electrical contact with body tissue. In other words, if the electrodes 160 are located in the non-porous region, e.g., masked region, the electrodes 160 are at least partially exposed on the outer surface 154 so that they are capable of making tissue contact, and if the electrodes 160 are located in porous region their ability for sensing or pacing is not impaired because the porous region provides good electrically conductive properties. Connection wires 162, 163 respectively connect the temperature sensors 159 and electrodes 160 to the cable.

Opaque markers 164 may also be integrally formed with the body 142 so that the physician can guide the device under fluoroscopy to the targeted site. Any high-atomic weight material is suitable for this purpose. For example, platinum or platinum-iridium may be used in the markers 164. Preferred placements of these markers 164 are at the distal tip and the center of the electrode structure 140, completely embedded within the body 142 or located on the inner surface 152 of the body 142.

Figure 10A:
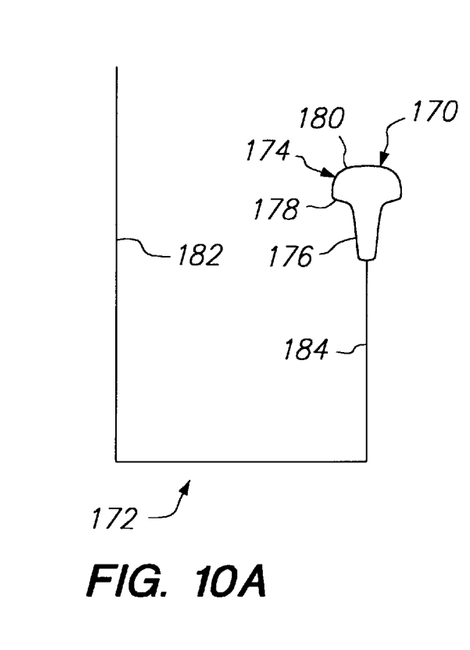
FIGS. 10A–10C are side elevational views of exemplary mandrels that may be used in manufacturing the electrode structure of the present invention.
Figure 10B:
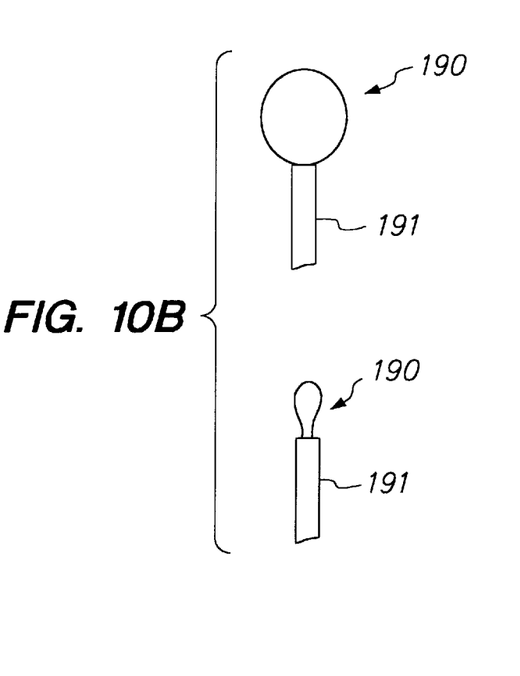
Figure 10C:
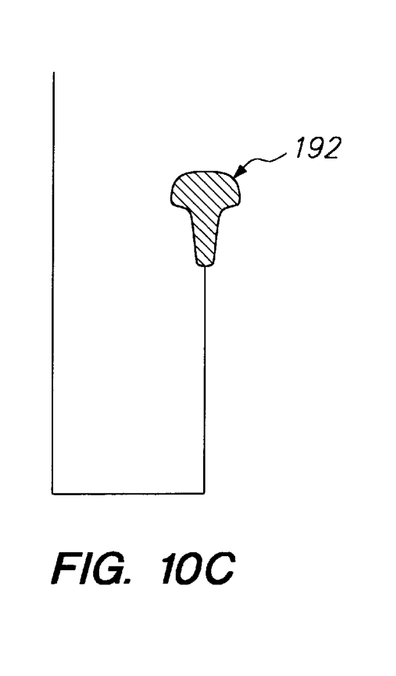

With reference to FIGS. 10A–10C, a number of methods for manufacturing a three-dimensional electrode body of regenerated cellulose will now be described.

FIG. 10A illustrates a dissolvable mandrel 170 carried by a support frame 172. The mandrel 170 has a head portion 174 and a neck portion 176. The head portion has a proximal region 178 and a distal region 180. The head portion 174 and the neck portion 176 of the mandrel 170 have the same general shape as the head portion 84 and neck portion 90 of the body 82 illustrated in FIG. 5.

The support frame 172 is generally "U" shaped and includes a handle portion 182 that is manipulated by a user's hands and a support portion 184 that carries the mandrel 170.

The dissolvable mandrel 170 is formed onto the support portion 184 of the support frame 172 by injecting mandrel solution into a two-piece mold. After the mandrel solution solidifies, the molds are split apart, leaving the desired mandrel 170. The mold may be formed from two mating aluminum, clay, or other material blocks which are milled, pressed, or formed into the desired shape. The two blocks are clamped together during the mandrel forming process and incorporate an injection port for injecting the mandrel solution, i.e., venting ports for preventing bubble formation, and support ports for accommodating the support portion 184 of the support frame 172.

The mandrel 170 preferably has a generally pear or summer squash shape, as illustrated in FIGS. 5–9. To create the body 82 illustrated in FIGS. 6A and 6B, the mandrel 170 must have corresponding longitudinally disposed ridges and bulbous regions. The bulbous regions have longitudinal grooves therein to accommodate the support rib assembly 95.

Similarly, the mandrel 170 may include other specially configured recesses or protrusions to create a desired body geometry. For example, recessed portion 156 illustrated in FIG. 9A may be formed by creating a corresponding recessed portion in the distal region 180 of the mandrel 170. Ribs similar to the ribs 97 illustrated in FIG. 9A and 9B are preferably integrally formed with the body 142 by providing rib-shaped recesses or grooves in the mandrel 170 so that the formed body 142 includes ribs also made of regenerated cellulosic substance or ribs made of a different material, e.g., casing paper, encased within the cellulosic material.

The pacing electrode 72d and temperature sensor 74d illustrated in FIG. 9A at the distal tip of the regenerated cellulose body 142 may be incorporated into the mandrel 170 so that upon forming the regenerated cellulose body 142 a bond forms between the pacing electrode 72d and the distal portion of the body 142 surrounding the pacing electrode 72d. A mask such as a solid strip of flattened wire may be placed over the pacing electrode 72d and temperature sensor 74d prior to forming the body 142 to prevent these elements from being covered during the body forming process. After the mandrel 170 is dipped into the cellulosic substance, the mask is removed, exposing the pacing electrode 72d and temperature sensor 74d. The bond between the pacing electrode 72d and the immediate portion of the body 146 surrounding it may be strengthened by an affixant such as cyanoacrylate, or other mechanical bond, e.g., wrapping these portions together with a wire.

Operative elements such as temperature sensors 159, electrodes 160 and opaque markers 164, and other elements such as ring electrode/collar 60d, and balloon support 102d illustrated in FIG. 9 may be formed with the body 142. For example, the operative elements may be readily laminated in the body wall by supporting them by the mandrel 170 during the body forming process, similar to the lamination or encasement of the support rib assembly 95 within the body 142. The signal wires 162, 163 for the temperature sensors 159 and electrodes 160, respectively, are fed through the mandrel 170 or on the exterior surface of the mandrel 170 towards the neck portion 176, and ultimately through the guide tube 24 of the catheter 20 for connection to the cable 31. If any of the operative elements need to be exposed on the exterior surface of the body, a mask may be employed similar to that described above for the pacing electrode 72d and temperature sensor 74d at the distal tip.

The electrode or collar 60d, and balloon support 102d may be incorporated into the mandrel 170 so that the distal region 180 of the mandrel 170 mates with the tip of the balloon support 102d and the proximal region of the neck portion 176 mates with the proximal end of the electrode/collar 60d. Upon formation of the electrode body 142, a bond is created between the body 142 and the collar 60d at the proximal region of the neck portion 146 of the body 142 and the distal tip of the head portion 142 of the body. The electrode 60d may also have mechanical bonding means such as threaded fasteners (not shown) for screwing into an interior lumen of the distal portion of the catheter guide tube. The bond between the electrode body and the collar 60d and balloon support 102d may be strengthened by an affixant such as cyanoacrylate.

In a preferred embodiment of the method of manufacturing the electrode body using a dissolvable mandrel, the dissolvable mandrel 170 is made of polyethylene glycol. The polyethylene glycol mandrel 170 has a smooth, waxy exterior. Because of the smooth exterior of the mandrel 170, an adhesive primer coating is added to the exterior of the mandrel 170 for causing the cellulosic substance to adhere to the mandrel 170 in the dipping steps described below.

The primer coating may be applied over the mandrel 170 by dipping or spraying the mandrel 170 in or with a commercially available base primer. Preferably, the mandrel 170 is sprayed with Duro brand all-purpose spray adhesive manufactured by Loctite Corporation, North America Group, of Rock Hill, Conn. It will readily appreciated by those skilled in the art that similar primer coating materials may be used.

After applying the primer coating, the mandrel 170 is dipped into a viscose or cellulosic substance, head portion 174 first. The cellulosic substance is viscose (cellulose xanthate), which is sold by Viskase Corporation of Chicago, Ill. Cellulose xanthate is a form of solubilized cellulose derivative that is dissolved in a sodium hydroxide solution.

The mandrel 170 is handled at the handle portion 182 of the support frame 172. The mandrel 170 may be dipped into the viscose solution manually or automatically. Automatic dipping by an automated dipping apparatus at a controlled dipping rate is preferred for achieving more repeatable results.

The thickness of the cellulosic substance is controlled by the viscosity of the solution and the dipping rate, and a different viscosity of the solution can be achieved by diluting it with sodium hydroxide solution. A variable wall thickness can be achieved by varying the extraction rate during the dipping process. The slower the extraction rate, the thinner the wall thickness, and the faster the extraction rate, the thicker the wall thickness.

Because the shape of the mandrel 170 and gravity causes the cellulosic substance to collect at the distal region 180 of the head portion 174, after dipping the mandrel, the distal region 180 is preferably tapped on a flat surface to remove substantially all the viscose solution on the distal region 180. As will be better understood below, this tapping step helps to ensure that the resulting electrode body has a uniform thickness, i.e., not too thick at the distal region of the head portion.

After the tapping step, the cellulosic substance remaining on the mandrel 170 is coagulated in a 15% wt./wt. sodium sulfate solution to secure and solidify the viscose solution on the mandrel 170.

Next, the mandrel 170 is re-dipped into the cellulosic substance, neck portion 176 first. The cellulosic substance used in the redipping or second dipping step may be the same or a different cellulosic substance from that used in the first dipping step. Re-dipping the mandrel 170 neck portion 176 first achieves the proper thickness of viscose solution on the mandrel 170.

After re-dipping the mandrel 170, the viscose solution is regenerated in a weak 0.01% wt./wt. sulfuric acid ($H_2SO_4$) solution for approximately 45 minutes. The sulfuric acid converts the xanthate of the cellulose xanthate back into the cellulose structure. The term regenerated cellulose refers to cellulose which has been converted from a solubilized cellulose derivative back into a pure cellulose structure. This regeneration process creates micro-size pores in the coating that are large enough to allow ionic transport, yet small enough to prevent the ingress of blood cells, infectious agents such as viruses and bacteria, and large biological molecules such as proteins. It will readily appreciated by those skilled in the art that similar regeneration solutions may be used.

Materials other than regenerated cellulose that are mechanically robust and that have suitable characteristics could be used for the coating material. Hydrophilic materials that have effective pore sizes from 500 to 500,00 Daltons with a porosity of 1–10% and which are biocompatible could be effective. Some types of hydrogels, such as those used for disposable contact lenses are good candidate materials. Plastic materials that have additives to make them semiconductive could also be used. The loaded plastic would need to have a resistivity in the range of about 200–2,000 ohm-cm, and would need to be appliable in very thin films to the mandrel 170.

After the cellulose is regenerated, it is rinsed with tap water to remove acid residuals and sulfur compounds. An oxidizing agent, e.g., bleach, may be added to the rinse water to accelerate the removal of sulfur compounds. It will readily appreciated by those skilled in the art that similar oxidizing agents may be used.

After the cellulosic substance is regenerated, it is fully cured in a low humidity environmental chamber at approximately 35° C. for approximately one hour, forming a regenerated cellulose body.

In order to remove the mandrel 170 regenerated from the cellulosic substance, the mandrel 170 and regenerated cellulosic substance are placed in a hot water bath at approximately 85° C. for approximately 30 minutes. The hot water bath causes the mandrel 170 to dissolve.

After the mandrel 170 dissolves, the regenerated cellulose body is removed from the water and dried.

Next, the regenerated cellulose body is positioned on a generally cylindrical mandrel having a diameter less than the diameter of the neck portion of the body. The regenerated cellulose body is dipped, neck portion first, into a non-porous masking material up to the distal region of the head portion. The masking material preferably used contains from about 85% wt./wt. to 95% wt./wt., and preferably about 91% wt./wt. to 93% wt./wt., polyester-polyurethane aqueous dispersion such as Bayhydrol PR240™ made by the Bayer Corp., and 5% wt./wt. to 15% wt./wt., and preferably about 4% wt./wt. To 6% wt./wt., polyfunctional aziridine cross linker such as cross linker CX-100™ made by Zeneca Resins in Wilmington, Mass. It will readily appreciated by those skilled in the art that similar masking materials may be used.

The masking material is cured by placing the regenerated cellulose body with masking material in an environmental chamber at approximately 110° C. for approximately one hour. The non-porous mask prevents ionic transport of electrical energy through the areas of the regenerated cellulose body covered by the mask.

It is preferable to make the regenerated cellulose flexible when dry, and to do so, moisture may be reintroduced into the regenerated cellulose body by placing the body into an environmental chamber and setting the environmental chamber to a high humidity. Alternatively, a small quantity of a material such as glycerol may be applied to the body, and the hydroscopic nature of the glycerol will hydrate the cellulosic substance to create sufficient flexibility.

In an alternative embodiment of the method of manufacturing the electrode using a dissolvable mandrel, the dissolvable mandrel 170 is made of a gelatin such as gelatan-type B-VG-100BLOOM made by Vyse Gelation Co. in Schiller Park, Ill.

The mandrel 170 is formed in the above-mentioned two-piece mold in a refrigerated environment. The mandrel 170 is preferably maintained in a refrigerated environment until the mandrel 170 is ready to be used for regenerated cellulose body formation. If the mandrel 170 is not refrigerated, water may evaporate from the gelatin mandrel, changing the dimension of the mandrel.

The dipping and curing process for the dissolvable gelatin mandrel is the same as that described above for the polyethylene glycol mandrel.

Mandrel materials such as polyethylene glycol and gelatin are desirable because they allow the regenerated cellulose body to be formed into a desired three-dimensional body shape. A polyethylene glycol mandrel is preferable over a gelatin mandrel because water evaporation is not a problem with polyethylene glycol.

With reference to FIG. 10B, an alternative method of manufacturing an electrode body will now be described. FIG. 10B illustrates an inflatable mandrel balloon 190 on a catheter guide tube 191, i.e., Swan Ganz catheter. The mandrel 190 is preferably made of latex, but may be made from Teflon or a similar material. The mandrel 190 can be expanded using gas or liquid into the general geometry desired for the body.

The dipping and curing process for the inflatable mandrel 190 is the same as that described above for the polyethylene glycol mandrel, except the mandrel balloon 190 is separated from the regenerated cellulose body by deflating the mandrel 190 instead of dissolving the mandrel.

In an alternative embodiment of the method of manufacturing the electrode body, a microporous braided structure 192 is provided around a mandrel such as one of the dissolvable mandrels, the balloon mandrel, or a glass mandrel. The braided structure 192 includes a mesh having the desired pore size and porosity. The structure 192 is fabricated from a material such as nylon, polyester, polyethylene, polypropylene, fluorocarbon, fine diameter stainless steel, or similar fiber.

If a conductive material such as stainless steel is used, the wire may also be used to deliver RF current from the generator to the body surface. The use of woven materials is advantageous because woven materials are very flexible as small diameter fibers can be used to weave the mesh. By using woven materials, uniformity and consistency in pore size also can be achieved. The three-dimensional structure may be formed from a braided tubing having an open proximal end and distended section with an open distal end, where the open distal end is sewn or welded closed.

The mandrel is separated from the braided structure 192 and is dipped into a cellulosic substance such as that previously described and allowed to cure. The wire or fiber separation for the braided structure would be small enough to enable the viscous cellulosic substance to adhere and cure, yet large enough not to interfere with the ionic flow required to produce a current path from the interior of the body to tissue contacting the exterior of the body.

After dipping the braided structure 192, the viscose material is regenerated in a weak 0.01% wt./wt. sulfuric acid ($H_2SO_4$) solution for approximately 45 minutes.

Alternatively, the mandrel 190 and braided structure 192 are dipped in the cellulosic substance. The cellulosic substance is cured and regenerated. Then, the mandrel 190 is separated from the braided structure 192.

After the cellulose is regenerated, it is rinsed with water, and cured in a low humidity environmental chamber at approximately 35° C. for approximately one hour.

Subsequently, a non-porous masking material is applied to the neck portion and proximal region of the head portion of the body in the manner described above and cured at approximately 110° C. for approximately one hour.

Alternatively, the dipping and curing process described above with respect to the polyethylene glycol mandrel 170 may be performed.

The braided structure gives the electrode body improved tensile strength and burst strength, and reduces the tendency to develop pin holes in the body.

The above-described methods of manufacturing a three-dimensional electrode structure produce a three-dimensional electrode body made of regenerated cellulose with a specific geometry that was not achievable in the past. The ability to produce a specific three-dimensional regenerated cellulose body allows all the advantages that regenerated cellulose offers and the advantages of a specific three-dimensional electrode structure, namely, the ability to create lesions having a specific geometry.

It will be readily understood by those skilled in the art that other methods may be employed to manufacture the electrode body such as, but not by way of limitation, injecting a cellulosic substance into the interior lumen of a glass mandrel in the shape of the electrode body followed by chemically etching the mandrel so that the cured cellulosic material remains, and dipping the exterior of a glass mandrel in the shape of the electrode body followed by chemically etching the mandrel so that the cured cellulosic material remains.

With reference to FIGS. 11–16, a method of assembling the electrode structure illustrated in FIGS. 8A and 8B in accordance with a preferred embodiment of the invention will now be described.

Figure 11A:
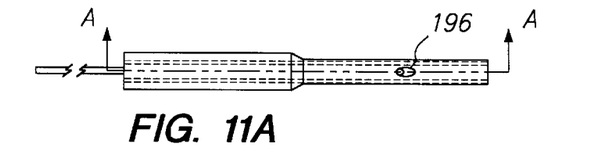
FIGS. 11A and 11B are a top plan view and a cross-sectional view, respectively, of a balloon support illustrated in FIG. 8A, and illustrate a step in assembling the electrode structure illustrated in FIG. 8A.
Figure 11B:
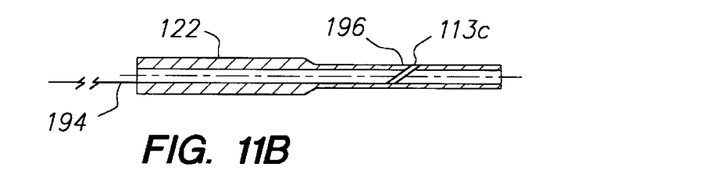

With reference to FIGS. 11A and 11B, the temperature sensor 113c is added to the balloon support 122. The temperature sensor 113c preferably comprises a thermocouple having a pair of lead wires 194 extending therefrom. The temperature sensor 113c is affixed within a window 196 of the balloon support 122 with an affixant such as cyanoacrylate so that the temperature sensor 113c is at least partially exposed.

Figure 12A:
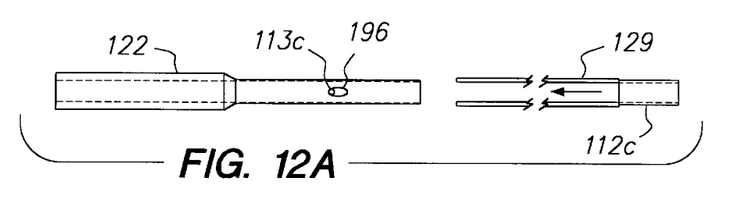
FIGS. 12A and 12B are a top plan view and a cross-sectional view, respectively, of the balloon support and electrode illustrated in FIG. 8A, and illustrate another step in assembling the electrode structure illustrated in FIG. 8A.
Figure 12B:
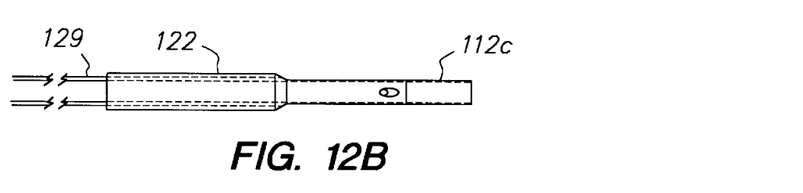

With reference to FIGS. 12A and 12B, the electrode 112c and lead wires 129 are slid over the distal portion 126 of the balloon support 122. The wires 129 fit into the laterally incurved sections 128, in opposite side of the balloon support 122 (FIG. 8B).

Figure 13A:
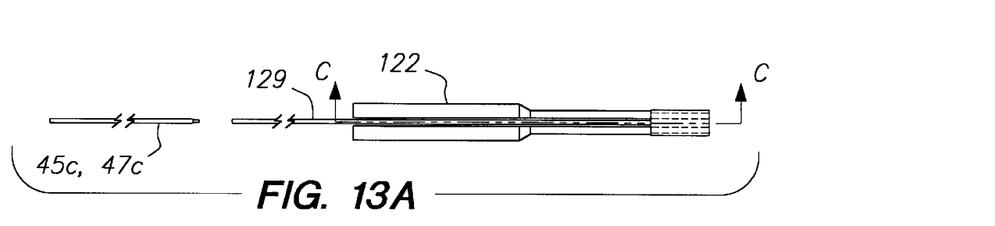
FIGS. 13A and 13B are a top plan view and a cross-sectional view, respectively, of the balloon support, electrode, and lumens illustrated in FIG. 8A, and illustrate an additional step in assembling the electrode structure illustrated in FIG. 8A.
Figure 13B:
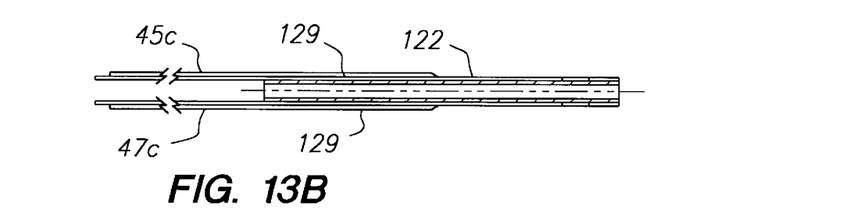

With reference to FIGS. 13A and 13B, the lumens 45, 47 are fit into the laterally incurved sections 128 (FIG. 8B),over the wires 129, and affixed there to 122 with an affixant such as cyanoacrylate.

Figure 14:
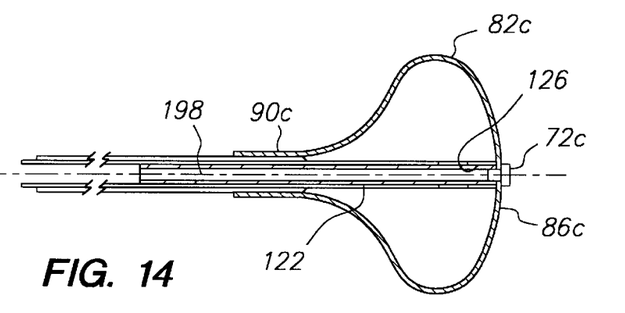
FIG. 14 is a cross-sectional view of the balloon support, electrode, lumens, and body of the electrode structure illustrated in FIG. 8A, and illustrates a further step in assembling the electrode structure illustrated in FIG. 8A.

With reference to FIG. 14, the body 82c and pacing electrode 72c, including the associated temperature sensor, are added to the balloon support 122. The balloon support 122 is inserted within the body 82c or the body 82c is placed over the balloon support 122. An inner wall of the neck portion 90c is affixed to an outer wall of the balloon support 122 with an affixant such as cyanoacrylate. The bond between the pacing electrode 72c and the distal region 86c of the body 82c is created or reaffirmed 122, if a bond exists, with an affixant such as cyanoacrylate. The bottom portion of pacing electrode 72c is affixed to the distal region 126 of the balloon support 122 also with an affixant such as cyanoacrylate. Wires 198 from the pacing electrode 72c and associated temperature sensor are threaded through the balloon support 122 for connection to the cable 31.

Figure 15:
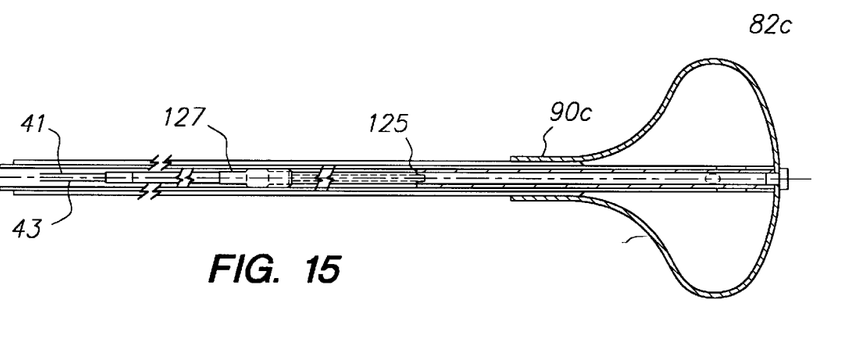
FIG. 15 is a cross-sectional view of the balloon support, electrode, lumens, body, and distal portion of the steering wire assembly of the electrode structure illustrated in FIG. 8A, and illustrates an additional step in assembling the electrode structure illustrated in FIG. 8A.

With reference to FIG. 15, the distal portion 125 of the steering wire assembly 127 is affixed to the proximal portion 124 of the balloon support 122 with an affixant such as cyanoacrylate.

Figure 16:
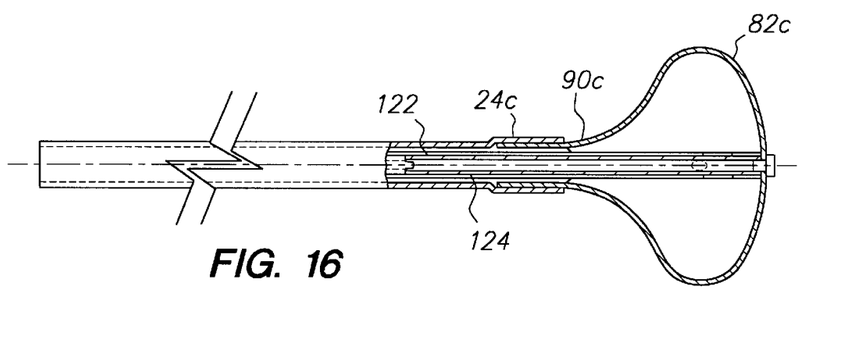
FIG. 16 is a cross-sectional view of the electrode structure illustrated in FIG. 8A and a distal portion of the catheter, and illustrates a still further step in assembling the electrode structure illustrated in FIG. 8A.

Finally, with reference to FIG. 16, the guide tube 24c is installed over the proximal portion 124 of the balloon support 122 and the neck portion 90c of the body 82c, and affixed to the outer wall of the neck portion 90c with an affixant such as cyanoacrylate.

It will be readily understood by those skilled in the art that certain features and elements described above may be incorporated into other embodiments even though not specifically described with respect to that embodiment. For example, the balloon support described in conjunction with FIGS. 7–9 and 11–16 may be replaced with or include a biasing device and/or tissue evaluating mechanism such as that described in FIGS. 2–5. Moreover, although this invention has been described in terms of certain preferred embodiments, other embodiments apparent to those of ordinary skill in the art are also within the scope of this invention. Accordingly, the scope of the invention is intended to be defined only by the claims that follow.

We claim:

1. A method of manufacturing a cellulosic structure, comprising:
   providing a mandrel having a head portion and a neck portion, the head portion having an outer circumference greater than the neck portion;
   dipping the mandrel into a cellulosic substance head portion first;
   dipping the mandrel into a cellulosic substance neck portion first;
   curing the cellulosic substance on the mandrel; and
   separating the mandrel from the cured cellulosic substance.

2. The method of claim 1, wherein the mandrel is made of gelatin.

3. The method of claim 1, wherein the mandrel is made of polyethylene glycol.

4. The method of claim 1, wherein the mandrel comprises an expandable-collapsible structure, and wherein the mandrel is separated from the cellulosic substance by collapsing the mandrel.

5. The method of claim 1, further comprising regenerating the cured cellulosic substance.

6. The method of claim 5, wherein the cellulosic substance is cured in an acid bath.

7. The method of claim 1, further comprising freezing the mandrel prior to dipping the mandrel into the cellulosic substance.

8. The method of claim 1, further comprising coating the mandrel with an adhesive prior to dipping the mandrel into the cellulosic substance.

9. The method of claim 1, further comprising coagulating the cellulosic substance on the mandrel in a salt solution after the first dipping.

10. The method of claim 1, wherein separating the cellulosic substance from the mandrel includes dissolving the mandrel in heated water.

11. The method of claim 1, wherein the head portion of the mandrel includes a plurality of channels, the method further comprising disposing a reinforcing support structure in one or more of the channels prior to dipping the mandrel into the celulosic substance, such that the support structure is embedded at least partially within the cured cellulosic substance.

12. The method of claim 1, wherein the head portion of the mandrel includes a generally flat distal region having a recessed area, the method further comprising placing an operative element in the recessed area prior to dipping the mandrel into the cellulosic substance, such that the operative element is embedded at least partially within the cured cellulosic substance.

13. The method of claim 1, further comprising masking at least a portion of the cured cellulosic substance with a non-porous masking primer.

* * * * *